United States Patent [19]

Tseo

[11] Patent Number: 4,506,691
[45] Date of Patent: Mar. 26, 1985

[54] THREE-WAY VALVE FOR AUTOMATIC SEQUENCING OF FLUID FLOW

[75] Inventor: Gus G. Tseo, San Diego, Calif.

[73] Assignee: Warner-Lambert Company, Morris Plains, N.J.

[21] Appl. No.: 594,135

[22] Filed: Mar. 28, 1984

[51] Int. Cl.³ .............................................. F16K 11/00
[52] U.S. Cl. ........................................ 137/1; 137/113; 137/606; 604/91
[58] Field of Search ............... 137/602, 606, 322, 113, 137/1; 251/149.7; 604/82, 83, 91; 222/129, 135, 136, 145

[56] References Cited

U.S. PATENT DOCUMENTS

| | | | |
|---|---|---|---|
| 2,312,686 | 3/1943 | Campbell | 137/113 |
| 2,854,027 | 9/1958 | Kaiser et al. | 604/83 X |
| 3,057,370 | 10/1962 | Hamilton | 137/315 |
| 3,280,834 | 10/1966 | Zahuranec | 137/606 X |
| 3,352,531 | 11/1967 | Kilmarx | 251/149.6 |
| 3,353,724 | 11/1967 | Johnston | 137/322 X |
| 3,385,301 | 5/1968 | Harautuneian | 128/349 |
| 3,799,171 | 3/1974 | Patel | 128/349 |
| 3,965,910 | 6/1976 | Fischer | 128/349 |
| 3,985,133 | 10/1976 | Jenkins et al. | 604/67 |
| 4,159,102 | 6/1979 | Fallon et al. | 137/322 X |

Primary Examiner—Martin P. Schwadron
Assistant Examiner—Stephen M. Hepperle
Attorney, Agent, or Firm—Neil K. Nydegger

[57] ABSTRACT

A three-way valve for automatic sequencing of fluid flow from a syringe into an IV administration set comprises a housing which forms a fluid chamber having a first and a second inlet and an outlet. A sleeve having a fluid passageway normally closed by a check valve is slidably disposed within the fluid chamber for reciprocal movement between a first position and a second position for respective fluid sealing engagement with the first and second inlets. With the sleeve in the second position, fluid flows through the chamber from the first inlet to the outlet. Engagement of a syringe with the second inlet urges the sleeve into the first position to permit fluid flow from the syringe into the second inlet and through the chamber to the outlet. Upon emptying of the syringe, the syringe plunger seals the second inlet and urges against a probe that opens the check valve to permit resumption of fluid flow from the first inlet to the outlet.

21 Claims, 5 Drawing Figures

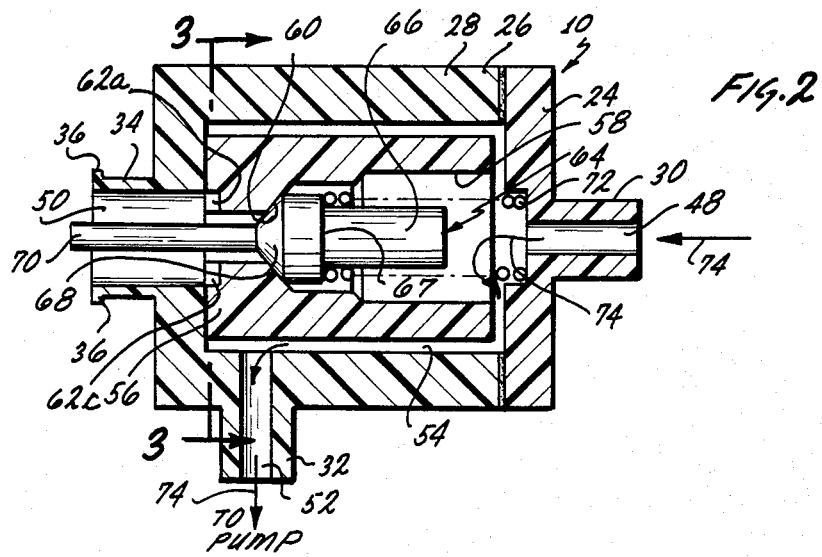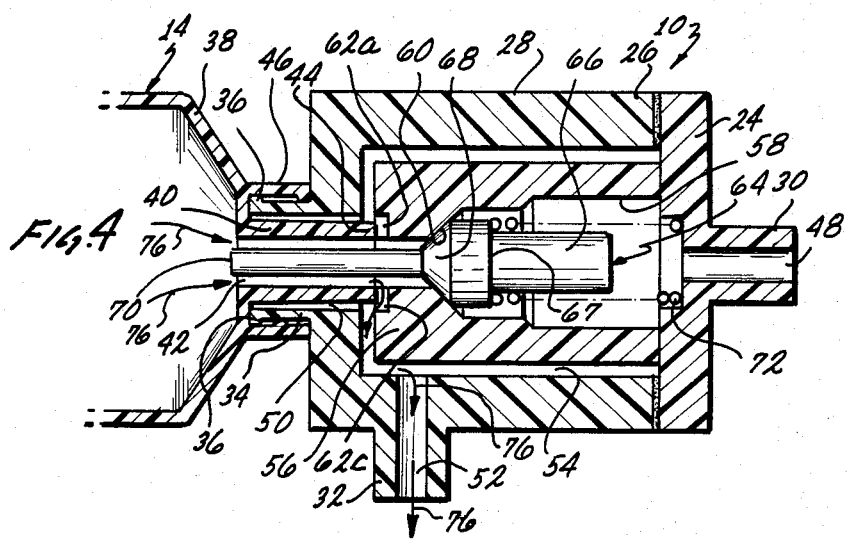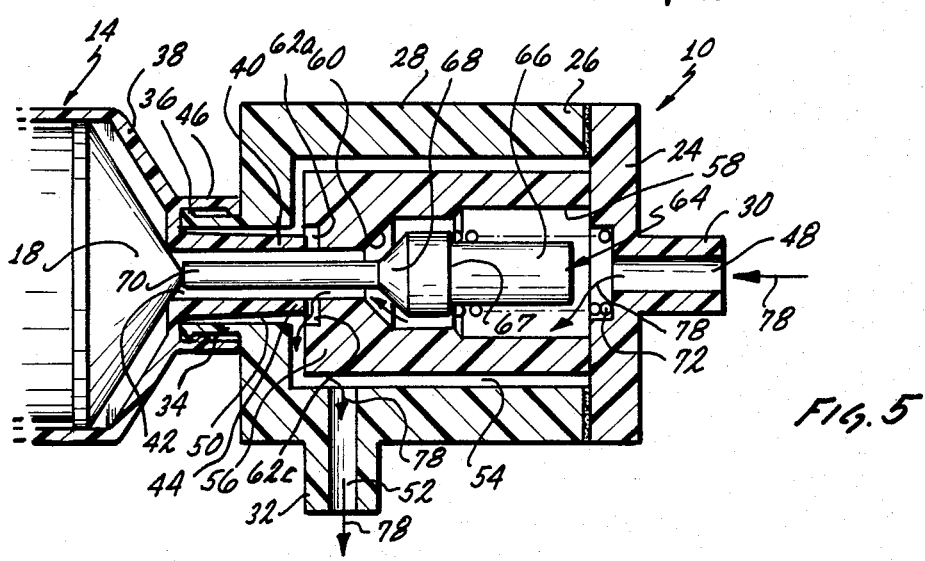

THREE-WAY VALVE FOR AUTOMATIC SEQUENCING OF FLUID FLOW

BACKGROUND OF THE INVENTION

This invention relates generally to a three-way valve designed for use with an IV fluid pumping system. Specifically, this invention pertains to a three-way valve which allows continuous fluid flow to a patient during interruption of fluid flow from the original source by permitting sequential access of a second fluid source into the existing fluid flow line with an automatic return to the original source after the pumping of fluid from the second source is completed. This invention is particularly, but not exclusively, useful for the sequencing of fluid from a syringe into a fluid flow pumping system used in an IV infusion.

DESCRIPTION OF THE PRIOR ART

The use of volumetric pumps to assist in the infusion of medications to patients is well established in the medical field. Several devices have been proposed for this purpose. For example, U.S. Pat. No. 3,985,133 to Jenkins, which is assigned of record to the assignee of the present invention, claims and discloses a volumetric pump which accurately infuses medications to a patient. Such systems, however, are typically designed for the infusion of medications from a single fluid source. Thus, whenever an additional medical fluid needs to be infused, either the pump must be temporarily shut down while the fluid container in the existing IV system is changed or a separate IV system must be set up. In either case, there may be unacceptable delays. Such delays, however, can be avoided if the new medical fluid can be introduced into the existing fluid delivery system without disassembling or shutting down the existing system.

Several valving devices have been proposed in the prior art for diverting fluid flow from one path to another. One such valve is the manually-operable three-way valve device disclosed in U.S. Pat. No. 3,057,370 to Hamilton. Other valves such as the check valve disclosed in U.S. Pat. No. 3,352,531 to Kilmarx have been proposed which are opened by cooperation with an external structure, such as the tip of a syringe, to establish a fluid passageway. Additional examples of such devices in the medical field are U.S. Pat. No. 3,385,301 to Harautuneian and U.S. Pat. No. 3,799,171 to Patel. Another depressor activated device is the valve disclosed in U.S. Pat. No. 3,965,910 to Fischer which defines a separate passageway for the addition of a second fluid into an existing fluid pathway during engagement of the depressor. There is, however, still the need for an automatic return to the normal fluid flow of the pre-existing fluid pathway when flow from the second fluid source has been completed.

Accordingly, it is an object of the present invention to provide a three-way valve which is simple in operation and allows for easy engagement of a second fluid source into a pre-existing fluid flow line. Another object of the present invention is to provide a cost effective disposable valve for use with a pumping system that will permit the accurate delivery of fluid from either of two separate fluid sources. It is still another object of the present invention to provide a valve which will automatically re-establish the pre-existing fluid pathway after the introduction of fluid from a second source has been completed.

SUMMARY OF THE INVENTION

The preferred embodiment of the novel three-way valve for use with an IV pump comprises means for the continuous sequentially alternating infusion of fluids from a fluid container and a syringe with an automatic return to the fluid container. More specifically, the novel three-way valve comprises a housing which defines a fluid chamber having a first and a second inlet for the access of fluids from the two separate sources and an outlet. A sleeve assembly, comprising a hollow tubular-shaped sleeve and a check valve positioned to prevent fluid flow through the sleeve, is slidably disposed within the fluid chamber for movement between a first position and a second position. A spring ordinarily urges the sleeve assembly into the second position for fluid sealing engagement with the second inlet. With the sleeve assembly in the second position, a fluid pathway through the housing is defined from the first inlet to the outlet.

Engagement of a syringe with the three-way valve, by insertion of the syringe tip into the second inlet, overcomes the spring bias to move the sleeve assembly from the first position to the second position. This movement urges the sleeve assembly into fluid sealing engagement with the first inlet. With the sleeve assembly in the second position, a fluid pathway is defined from the second inlet to the outlet. When the pumping of fluid from the syringe is completed, the syringe plunger contacts a probe extending from the check valve and causes the check valve to open. Simultaneously with the opening of the check valve, the syringe plunger engages in fluid sealing contact with the second inlet. In this configuration the valve housing re-establishes a fluid passageway from the first inlet to the outlet.

The novel features of this invention as well, as the invention itself, both as to its organization and operation will be best understood from the accompanying drawings, taken in conjunction with the accompanying description, in which similar reference characters refer to similar parts, and in which:

BRIEF DESCRIPTION OF THE DRAWINGS

FIG. 2 is a cross-sectional view of a portion of the three-way valve as seen on line 2—2 in FIG. 1 without the syringe attached;

FIG. 4 is a cross-sectional view of a portion of the three-way valve as seen on line 2—2 in FIG. 1 with the three-way valve engaged with a syringe during fluid flow from the syringe; and FIG. 5 is a cross-sectional view of a portion of the three-way valve as seen on line 2—2 in FIG. 1 engaged with a syringe after fluid flow from the syringe has been completed.

DESCRIPTION OF THE PREFERRED EMBODIMENT

Figure 1:
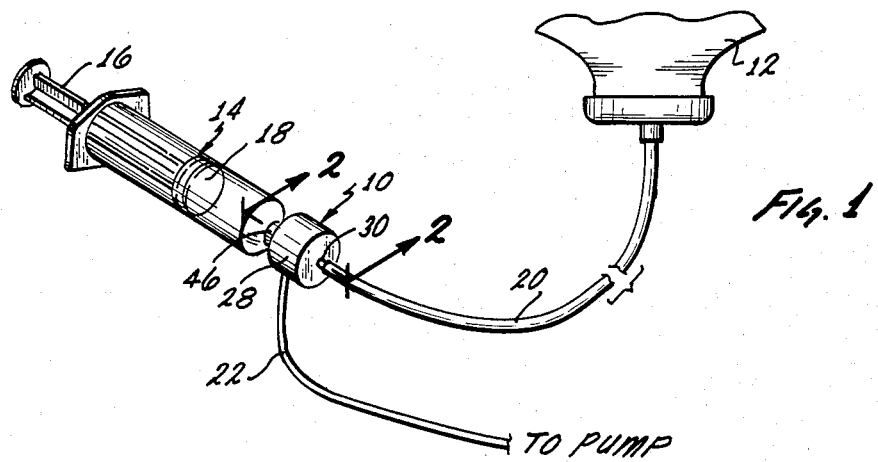
FIG. 1 is a perspective view of the three-way valve shown connected with two separate fluid sources, one of which is a syringe.

Referring initially to FIG. 1, a three-way valve generally designated 10 is shown connected for fluid communication with a standard IV bottle 12 by an IV tube 20. Also shown connected for fluid communication with three-way valve 10 is a syringe 14. As shown in FIG. 1, IV bottle 12, syringe 14 and three-way valve 10 are connected in a manner so that fluid from either bottle 12 or syringe 14 can be directed through three-way valve 10 and into IV tube 22 for flow to a fluid volumetric pump (not shown).

In FIG. 2 it is seen that three-way valve 10 includes a housing 28 formed by joining an end portion 24 with a base portion 26 to establish a fluid chamber 54. It should be appreciated that the joining of end portion 24 with base portion 26 may be accomplished by any means well known in the art, such as by solvent bonding or ultrasonic bonding. Formed onto end portion 24 is a fitment 30 which defines a fluid inlet 48 into fluid chamber 54. Also, for reasons which will subsequently become apparent, fitment 30 is adapted for fluid fluid sealing engagement with IV tube 20.

Still referring to FIG. 2, it is seen that base portion 26 is formed with a fitment 32 which defines a fluid outlet 52 from fluid chamber 54. Fitment 32 is adapted for fluid sealing engagement with IV tube 22. Base portion 26 is also formed with a fitment 34 which defines a fluid inlet 50 into fluid chamber 54. Formed onto the external periphery of fitment 34 is a two-point partial thread 36 that permits screwable engagement of three-way valve 10 with syringe 14. It should be understood that fitment 34 may be a standard luer lock.

Slidably disposed in fluid chamber 54 is a hollow tubular-shaped flexible sleeve 56 forming a fluid passageway 58 therethrough. In the preferred embodiment, sleeve 56 is made from an elastomeric material suitable for fluid sealing engagement with base portion 26 and end portion 24. Within fluid passageway 58 is a shoulder portion 60. As can also be appreciated with reference to FIG. 2, the sleeve 56 is dimensioned so that its length is slightly less than the longitudinal dimension of the fluid chamber 54 to permit slidable reciprocation of the sleeve 56 within the fluid chamber 54.

As seen in FIG. 2, a check valve 64 is disposed within the passageway 58 of sleeve 56. The check valve 64 is formed with a stem portion 66 of slightly reduced cross-sectional area to define a lip 67. Also formed onto check valve 64 is an abutment 68 which is adapted for fluid sealing engagement with shoulder 60 of sleeve 56. As previously discussed sleeve 56 is preferably made of an elastomeric material. Thus, abutment 68 of sleeve 56 is capable of fluid sealing engagement with valve 64. Also included in the structure of check valve 64 is a probe arm 70 which is an integral extension of the check valve 64 and is dimensioned to extend through fluid passageway 58 of sleeve 56 into inlet 50 of fitment 34 as shown in FIG. 2.

A spring 72 cooperating between the end portion 24 of housing 28 and lip 67 of check valve 64 urges the abutment portion 68 of check valve 64 into fluid sealing engagement with the shoulder 60 of sleeve 56. As can also be appreciated by reference to FIG. 2, the urging of spring 72 against check valve 64 also urges sleeve 56 into a fluid sealing engagement with base portion 26 of housing 28. This engagement prevents fluid from entering fluid chamber 54 through fluid inlet 50. As can be further appreciated by reference to FIG. 2, this engagement also causes probe arm 70 of check valve 64 to extend into inlet 50.

Referring now to FIG. 4, it is seen that syringe 14 includes an extension forming a fluid conduit 42. Also, extension 40 is dimensioned to be received within the inlet 50 of fitment 34. Fluid sealing engagement of the syringe 14 with three-way valve 10 is secured by a connector 46 that is adapted to threadably engage with thread 36 located on the external periphery of fitment 34. As seen in FIG. 4, both extension 40 and connector 46 of syringe 14 are integral extensions of the wall 38 of syringe 14. As is best shown in FIG. 4 and FIG. 5, the engagement of syringe 14 with three-way valve 10 causes extension 40 of syringe 14 to extend into inlet 50 of fitment 34 in a manner that permits probe arm 70 of check valve 64 to extend into extension 40 of syringe 14. It is important that probe arm 70 be of sufficiently reduced cross-sectional area, when compared with fluid conduit 42, to permit fluid communication from syringe 14 through the fluid conduit 42 even though probe arm 70 extends into fluid conduit 42.

Figure 3:
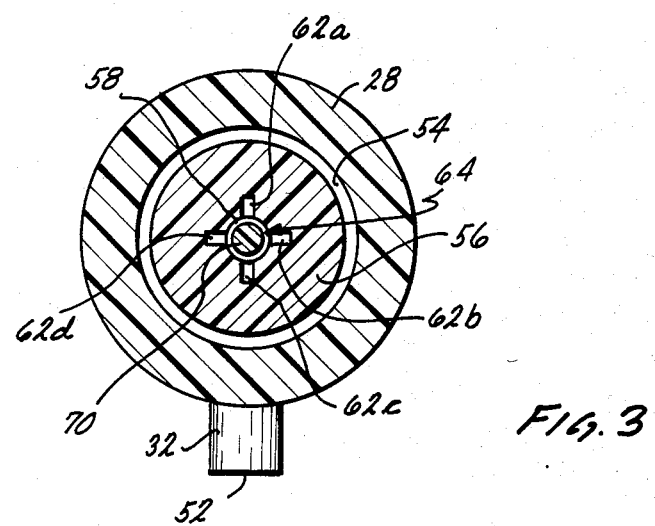
FIG. 3 is a cross-sectional view of a portion of the three-way valve as seen on line 3—3 in FIG. 2.

Referring now to FIG. 3, it is seen that passageway 58 in sleeve 56 has associated therewith the slots 62a, b, c and d which extend radially from the passageway 58 to form fluid pathways that are substantially perpendicular to the fluid passageway 58. For purposes which will become clearer during the subsequent discussion of the operation of three-way valve 10, slots 62a, b, c and d effectively prevent the establishment of a fluid seal between tip 44 of extension 40 and sleeve 56.

OPERATION

In its operation, the three-way valve 10 is primarily intended for use in a system for administering IV fluids to a patient. As seen in FIG. 1, such a system typically includes an IV bottle 12 in fluid communication with a volumetric pump (not shown). More specifically, bottle 12 is connected to an IV tube 20 which, in turn, is connected by any manner well known in the art to the three-way valve 10, and IV tube 22 is connected with outlet 52 of three-way valve 10 for the passage of fluid to an animate patient. A second fluid source, such as syringe 14, is pre-filled with a medicament in a customary manner according to the particular needs of the patient. The engagement of syringe 14 with three-way valve 10 is accomplished by the nurse or operator in a manner as shown in FIG. 4 or FIG. 5. As seen in these figures, extension 40 of syringe 14 is inserted into the inlet 50 of three-way valve 10 and syringe 14 is then rotated to engage connector 46 with thread 36 of fitment 34. As is best seen in FIG. 4, this connection between syringe 14 and three-way valve 10 causes the tip 44 of extension 40 to engage with sleeve 56 and unseat sleeve 56 from the base portion 26 of housing 28. This connection further urges sleeve 56 into fluid sealing engagement with the end portion 24 of housing 28 to provide a fluid tight seal between the sleeve 56 and end portion 24. As can be appreciated from FIG. 4, this also breaks the fluid seal over inlet 50 and instead provides a fluid tight seal over the inlet 48 into three-way valve 10. In this configuration a fluid passageway is established through fluid chamber 54 from inlet 50 to outlet 52. As can be appreciated from cross-reference between FIG. 3 and FIG. 4, as the tip 44 of extension 40 on syringe 14 contacts sleeve 56, a fluid passageway is created from fluid conduit 42 through the respective slots 62a, b, c and d on sleeve 56. The passage of fluid from conduit 42 into slots 62a, b, c and d then proceeds into fluid chamber 54 of housing 28. Also it can be appreciated in FIG. 4 that the above described engagement between syringe 14 and three-way valve 10 does not unseat the abutment 68 of check valve 64 from its fluid sealing engagement with shoulder 60 since abutment 68 continues to be urged against shoulder 60 by the spring 72 during the initial engagement of prefilled syringe 14 with three-way valve 10.

While the syringe 14 is engaged with three-way valve 10, the evacuation of fluid from syringe 14 by the pump (not shown) causes plunger 18 and its handle 16 to correspondingly advance into the syringe 14. It can be seen in FIG. 5 that when syringe 14 is emptied, plunger 18 urges against probe arm 70 to unseat check valve 64 from its fluid sealing engagement with sleeve 56. Simultaneously, plunger 18 is urged into fluid sealing engagement with extension 40 to prevent fluid flow through fluid conduit 42. It is preferred that plunger 18 be of an elastomeric material such as is found in commonly available syringes 14 to provide for the fluid seal.

In accordance with the above described operation, it can be appreciated that three-way valve 10 accomplishes the sequencing of fluid flow from bottle 12 and from syringe 14 in a manner graphically described by sequential consideration of FIG. 2, 4 and 5. In this sequence the three-way valve 10, prior to its connection with syringe 14, provides for a fluid path directly from bottle 12 through three-way valve 10 to a pump (not shown) as shown by the directional arrows 74 in FIG. 2. Thus, a fluid path is defined within three-way valve 10 from inlet 48 into fluid chamber 54 around the sleeve 56 and out of three-way valve 10 via outlet 52. Once syringe 14 is brought into operative engagement with the three-way valve 10, extension 40 acts to move sleeve 56 into a position to create a fluid seal between sleeve 56 and inlet 48 while simultaneously breaking the fluid seal between sleeve 56 and the inlet 50. Thus, a fluid path is established through three-way valve 10 as indicated by the directional arrows 76 in FIG. 4. More specifically, a fluid path is defined within three-way valve 10 from that portion of the passageway 58 which surrounds probe arm 70 through the slots 62a, b, c and d into chamber 54 for further flow from three-way valve 10 via outlet 52.

Finally, upon completion of the drawing of fluid from syringe 14, FIG. 5 shows that the plunger 18 contacts probe arm 70 to disengage check valve 64 from its fluid sealing engagement with the sleeve 56. At the same time, plunger 18 contacts with extension 40 to provide a fluid tight seal between the syringe 14 and inlet 50. Consequently, a fluid path is established through three-way valve 10 as indicated by directional arrows 78 in FIG. 5 which extends from inlet 48 into passageway 58, around check valve 64, out through the slots 62a, b, c and d, and into fluid chamber 54 for exit from the three-way valve 10 via outlet 52. It should be appreciated that fluid flow will continue along this path from bottle 12 through three-way valve 10 and to the pump (not shown) until the empty syringe 14 is disengaged from three-way valve 10. Upon disengagement of syringe 14 from three-way valve 10, the flow path from bottle 12 through three-way valve 10 and to the pump (not shown), as shown in FIG. 2, will be re-established.

While the particular three-way valve for sequencing of fluid as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the apended claims.

I claim:

1. A device for sequencing pumped fluid flow from separate sources in an IV administration set comprising:
    a housing formed with a fluid chamber and having a first inlet, a second inlet and an outlet;
    a sleeve having a fluid passageway therethrough disposed in said fluid chamber for movement between a first position and a second position;
    a check valve disposed in said passageway;
    first means to urge said sleeve into the first position for fluid sealing engagement with said second inlet to define a fluid pathway in said chamber between said first inlet and said outlet;
    second means to urge said sleeve from said first position into said second position for fluid sealing engagement with said first inlet to define a fluid pathway in said chamber between said second inlet and said outlet;
    third means operative while said sleeve is in said second position to close said second inlet and open said check valve to define a fluid pathway through said passageway from said first inlet to said outlet.

2. A device as recited in claim 1 wherein said check valve is slidably disposed in said passageway.

3. A device as recited in claim 2 wherein said passageway is formed with a shoulder and said check valve is formed with an abutment adapted for fluid sealing engagement with said shoulder.

4. A device as recited in claim 3 wherein said check valve is made of an elastomeric material.

5. A device as recited in claim 4 wherein said abutment of said check valve is urged into fluid sealing engagement with said shoulder of said sleeve by said first means.

6. A device as recited in claim 5 wherein said first means is a spring.

7. A device as recited in claim 6 further comprising a syringe having a plunger and a tip portion and an attachment means associated with said second inlet for connecting said syringe into fluid communication with said second inlet.

8. A device as recited in claim 7 wherein said second means is said tip portion.

9. A device as recited in claim 8 wherein said check valve further comprises an integral probe extending through said passageway and into said second inlet.

10. A device as recited in claim 9 wherein said third means is said plunger.

11. A device as recited in claim 10 wherein said plunger urges against said probe to disengage said abutment from said shoulder.

12. A device for sequencing pumped fluid flow comprising:
    a housing formed with a fluid chamber having a first inlet, a second inlet and an outlet positioned for fluid communication with said first and second inlets;
    a first fluid source engageable in fluid communication with said first inlet;
    a second fluid source engageable in fluid communication with said second inlet;
    a hollow sleeve slidably disposed in said fluid chamber for alternate fluid sealing engagement with said first and second inlets and having a fluid passageway in fluid communicating alignment with said first inlet;
    a shoulder formed in said passageway;
    a check valve slidably disposed in said passageway and urged into fluid sealing engagement with said shoulder to prevent fluid flow through said passageway;

first means for urging said sleeve into fluid sealing engagement with said second inlet;

second means for urging said sleeve into fluid sealing engagement with said first inlet and positioning said passageway in fluid communication with said first inlet; and third means for sealing said second inlet and breaking the fluid seal between said check valve and said shoulder to permit fluid flow through said passageway between said first inlet and said outlet.

13. A device as recited in claim 12 wherein said check valve is made of an elastomeric material.

14. A device as recited in claim 13 further comprising a probe integrally attached to said check valve for extending through said passageway and into said second inlet.

15. A device as recited in claim 14 wherein said first means urges said check valve into fluid sealing engagement with said shoulder.

16. A device as recited in claim 15 wherein said first means is a spring.

17. A device as recited in claim 16 wherein said second fluid source is a syringe having a plunger and a tip portion.

18. A device as recited in claim 17 wherein said second means is said tip portion.

19. A device as recited in claim 18 wherein said third means is said plunger.

20. A device as recited in claim 19 wherein said plunger urges against said probe to open said check valve.

21. A method for sequencing pumped fluid flow from separate sources in an IV administration set comprising the steps of:

a. engaging a first fluid source into fluid communication with a first inlet of a device comprising: a housing formed with a fluid chamber and having a first inlet, a second inlet and an outlet; a sleeve having a fluid passageway therethrough disposed in said fluid chamber for movement between a first position and a second position; a check valve disposed in said passageway; and first means to urge said sleeve into the first position for fluid sealing engagement with said second inlet to define a fluid pathway in said chamber between said first inlet and said outlet;

b. engaging a syringe with plunger into fluid communication with said second inlet to urge said sleeve from said first position into said second position for fluid sealing engagement with said first inlet to define a fluid pathway in said chamber between said second inlet and said outlet; and c. pumping fluid from said syringe until said plunger is in position to close said second inlet and open said check valve to define a fluid pathway through said passageway from said first inlet to said outlet.

* * * * *